United States Patent
Huang et al.

(10) Patent No.: US 7,730,767 B2
(45) Date of Patent: Jun. 8, 2010

(54) MICRO-SENSOR FOR SENSING CHEMICAL SUBSTANCE

(75) Inventors: Long Sun Huang, No. 28, Lane 60, Sec. 3, Keelung Rd., Da-an District, Taipei (TW); Chih-Kung Lee, Tainan (TW); Shih-Yuan Lee, Taipei (TW); Kuang-Chong Wu, Taipei (TW); Yi Kuang Yen, Taipei (TW)

(73) Assignee: Long Sun Huang, Taipei (TW)

( * ) Notice: Subject to any disclaimer, the term of this patent is extended or adjusted under 35 U.S.C. 154(b) by 230 days.

(21) Appl. No.: 11/976,683

(22) Filed: Oct. 26, 2007

(65) Prior Publication Data

US 2009/0019934 A1    Jan. 22, 2009

(30) Foreign Application Priority Data

Jul. 20, 2007    (TW) ................ 96126475 A

(51) Int. Cl.
*G01N 9/00* (2006.01)
(52) U.S. Cl. .................................... 73/31.05
(58) Field of Classification Search .............. 73/31.05
See application file for complete search history.

(56) References Cited

U.S. PATENT DOCUMENTS

| | | | | |
|---|---|---|---|---|
| 5,753,814 A | * | 5/1998 | Han et al. | 73/105 |
| 5,807,758 A | * | 9/1998 | Lee et al. | 436/526 |
| 7,260,980 B2 | * | 8/2007 | Adams et al. | 73/31.05 |
| 7,427,754 B2 | * | 9/2008 | Wang et al. | 250/306 |
| 2005/0074871 A1 | * | 4/2005 | Albert et al. | 435/287.2 |

* cited by examiner

*Primary Examiner*—Hezron Williams
*Assistant Examiner*—Rodney T Frank
(74) *Attorney, Agent, or Firm*—Stites & Harbison, PLLC; Juan Carlos A. Marquez, Esq.

(57) ABSTRACT

The invention discloses a micro-sensor for sensing a chemical substance. The micro-sensor according to the invention includes a substrate, a micro-cantilever, an electrode structure, and a measuring device. The micro-cantilever is formed on the substrate and has a capturing surface for capturing chemical substances. The electrode structure is for supplying an electrical field. The electrical field is disposed so as to assist the capturing surface in capturing chemical substances. The measuring device, coupled to the micro-cantilever, is for measuring a variation on a mechanical property of the micro-cantilever induced by the captured chemical substance and interpreting the variation on the mechanical property of the micro-cantilever into information relative to the chemical substance.

13 Claims, 3 Drawing Sheets

US 7,730,767 B2

MICRO-SENSOR FOR SENSING CHEMICAL SUBSTANCE

BACKGROUND OF THE INVENTION

1. Field of the Invention

The present invention relates to a micro-sensor and, more particularly, to a micro-sensor for sensing a chemical substance.

2. Description of the Prior Art

Due to stepping into the generation of advanced-age and uneven medical resource allocation, bio-chips have caused a great attention in all industries; as a result, educational institutes or industrial circles have put a large amount of fund and manpower into exploration and research.

In bio-sensing systems, many bio-sensing techniques have been developed maturely, which can systematically classify bio-sensing systems by means of various transducers. However, in the bio-sensing systems, an electron-type or a contact-type sensing system, e.g. a scanning probe microscopy or a scanning tunneling microscopy, has the drawbacks of disturbing reaction processes among organisms and possibly ruining living organisms on the bio-chips. Besides, conventional detection systems generally have the problems of high cost of purchase and maintenance, large-volume, low sensitivity, long measurement time, and great consumption of samples.

A micro-cantilever biosensor has the advantages of fluorescent labels-free, high sensitivity, low-cost fabrication, and a large amount of potential parallel detection. The micro-cantilever biosensor has been under a certain development for miniatures. The micro-cantilever of a micro-cantilever biosensor can be bended by a surface stress when a molecule film is produced. Alternatively, a mass change on the micro-cantilever can be measured by a resonance way.

In recent years, the research and development of the micro-cantilever biosensor can be divided into the surface stress induced by the molecule film, a hybrid reaction of DNA, a mutual reaction between protein-based antigen-antibody and detections of drugs and metal ions.

To fabricate a micro-cantilever biosensor, it is first to immobilize a probing protein on the micro-cantilever, then an analyte reaction is measured by use of the recognition of the probing protein and bio-molecules. However, in the step of immobilizing the probing protein on the micro-cantilever, a large amount of probing protein is often consumed to increase the cost of fabricating a bio-chip. Moreover, the consumption of probing protein usually costs the most in the manufacture cost of the bio-chip.

To solve the aforementioned problem, the main scope of the invention is to provide a micro-sensor for sensing a chemical substance.

SUMMARY OF THE INVENTION

One scope of the invention is to provide a micro-sensor for sensing a chemical substance.

According to an embodiment of the invention, the micro-sensor includes a substrate, a micro-cantilever, an electrode structure, and a measuring device.

The micro-cantilever is formed on the substrate and has a capturing surface for capturing chemical substances. The electrode structure is for supplying an electrical field. The electrical field is disposed so as to assist the capturing surface in capturing chemical substances. The measuring device is coupled to the micro-cantilever. The measuring device is for measuring a variation on a mechanical property of the micro-cantilever induced by the captured chemical substance and interpreting the variation on the mechanical property of the micro-cantilever into information relative to the chemical substance.

Compared to the prior art, with the electrical field provided by the electrode structure, the micro-sensor according to the invention can not only increase the immobilization efficiency of probing proteins on the capturing surface of the micro-cantilever but also reduce the consumption of biochemical samples.

The advantage and spirit of the invention may be understood by the following recitations together with the appended drawings.

BRIEF DESCRIPTION OF THE APPENDED DRAWINGS

DETAILED DESCRIPTION OF THE INVENTION

Figure 1A:
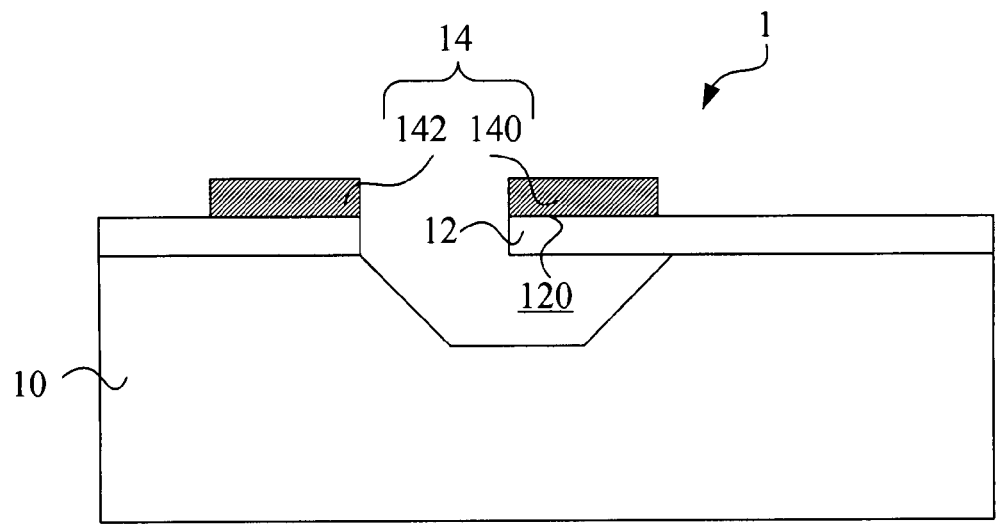
FIG. 1A is a micro-sensor for sensing a chemical substance according to one embodiment of the invention.

Please refer to FIG. 1A. FIG. 1A is a micro-sensor 1 for sensing a chemical substance according to one embodiment of the invention.

In practical applications, the chemical substance is a metal, a polymer, a biochemical molecule, or a micro-biochemical structure.

As shown in FIG. 1A, the micro-sensor 1 includes a substrate 10, a micro-cantilever 12, an electrode structure 14, and a measuring device (not shown in FIG. 1A).

In one embodiment, the substrate 10 can be formed of silicon, and the micro-cantilever 12 can be formed of $Si_3N_4$ or $SiO_2$, but not limited therein. Besides, in one embodiment, the micro-cantilever 12 structure can exhibit V-shaped.

The micro-cantilever 12 is formed on the substrate 10 and has a capturing surface 120 for capturing chemical substances.

In one embodiment, if the analyte is a chemical molecule, the capturing surface 120 can be covered with a chemical sensing film. The chemical sensing film can serve as an interface for bonding the chemical molecule and the micro-sensor 1, or serve as a reaction surface directly reacting with the analyte.

In one embodiment, if the analyte is a bio-molecule or a micro-biochemical structure, the capturing surface 120 can be covered with a bio-material sensing film. Therefore, an immobilization reaction occurs only between the bio-material sensing film and a selective bio-molecule or a micro-biochemical structure.

The electrode structure 14 is for supplying an electrical field. Bye use of the charged particles (e.g. positive or negative electric charge), the electrical field is disposed so as to assist the capturing surface 120 in capturing chemical substances.

In one embodiment, if the electrical field is a DC electrical field, the DC electrical field can assist the capturing surface 120 in capturing chemical substances. Further, the electrical field can be converted from the DC electrical field to an AC electrical field, and the AC electrical field can assist the chemical substance in escaping from the capturing surface 120. Therefore, the DC electrical field and the AC electrical field can enhance the efficiency of repeated sensing of the chemical substance.

In practical applications, the electrode structure 14 can include a first electrode 140 formed on the capturing surface 120 of the micro-cantilever 12, and a second electrode 142 formed on the substrate 10. In one embodiment, the first electrode 140 can be formed of gold, and the second electrode 142 can be formed of nickel, but not limited therein.

The measuring device is coupled to the micro-cantilever 12. The measuring device is for measuring a variation on a mechanical property of the micro-cantilever 12 induced by the captured chemical substance and interpreting the variation on the mechanical property of the micro-cantilever 12 into information relative to the chemical substance.

Figure 1B:
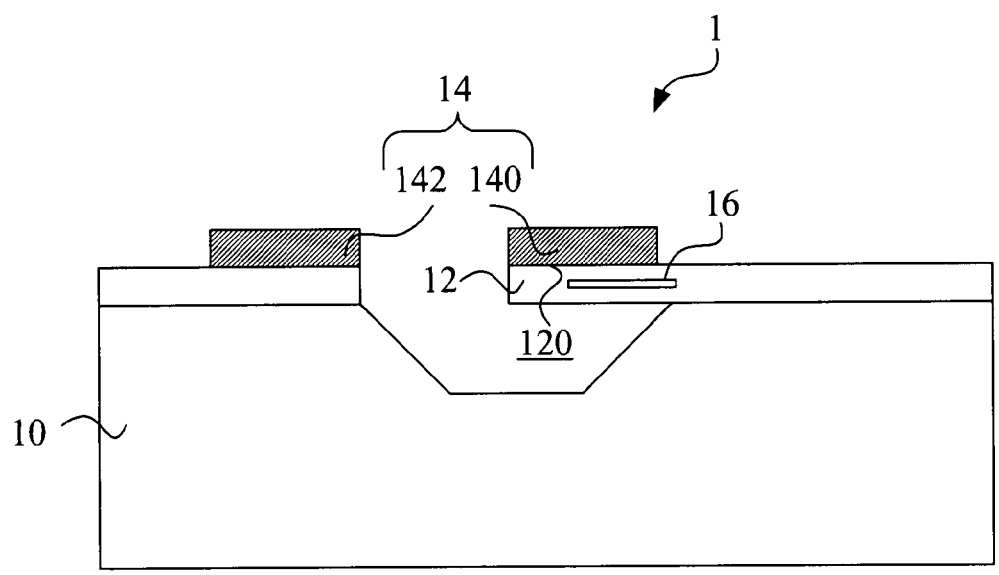
FIG. 1B is a micro-sensor according to another embodiment of the invention.
Figure 2:
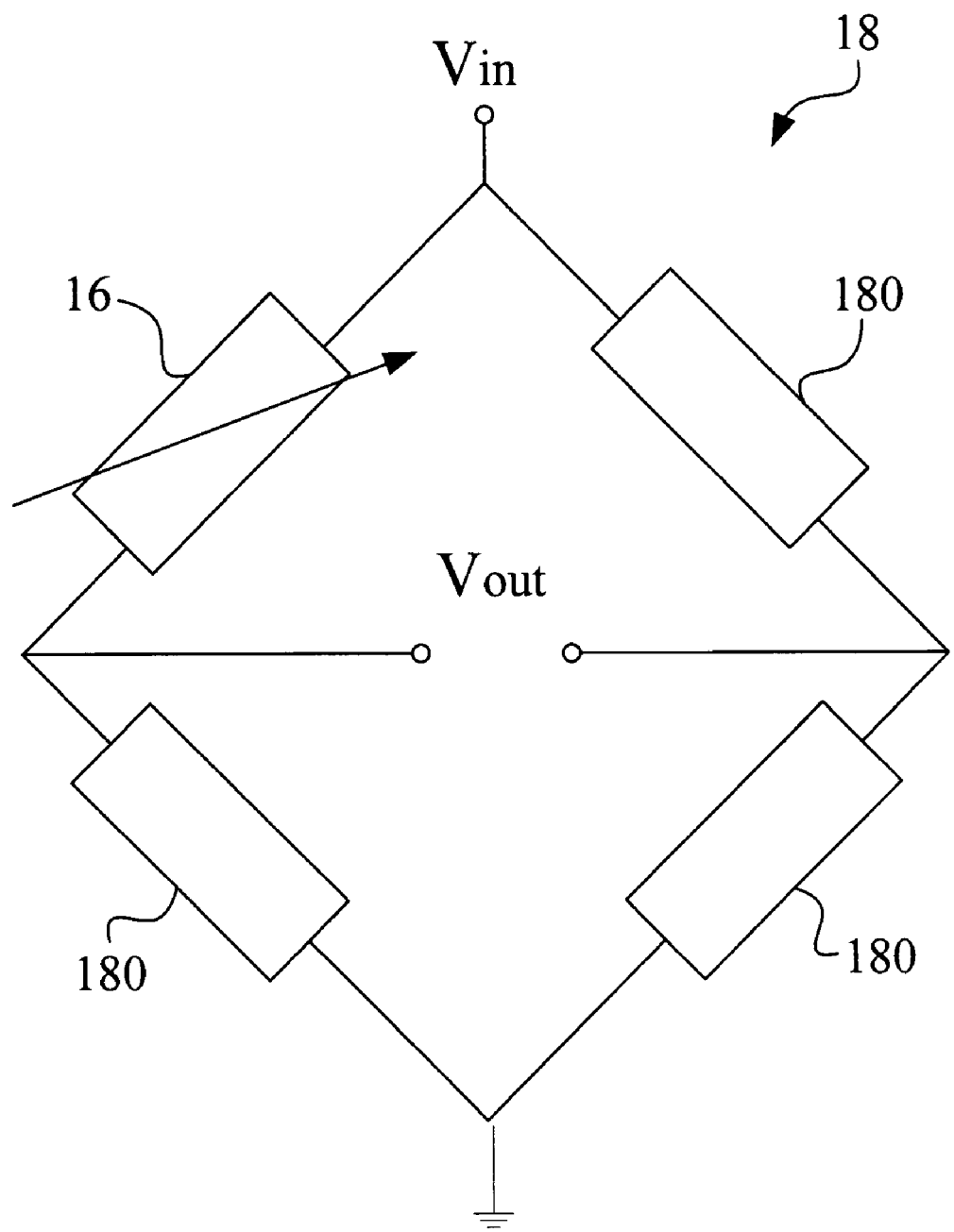
FIG. 2 is a schematic diagram of the measuring device.

Please refer to FIG. 1B and FIG. 2. FIG. 1B is a micro-sensor 1 according to another embodiment of the invention. FIG. 2 is a schematic diagram of the measuring device 18.

As shown in FIG. 1B, a portion of the micro-cantilever 12 is doped to form a piezoresistive element 16. As shown in FIG. 2, in one embodiment, at least one resistor 180 of the measuring device 18 and the piezoresistive element 16 constitute an electric bridge with which the measuring device 18 measures the variation on the mechanical property of the micro-cantilever 12. In detail, after the capturing surface 120 of the micro-cantilever 12 captures the chemical substance, the piezoresistive element 16 will generate a resistance value corresponding to a deflection variation of the micro-cantilever 12, i.e. the piezoresistive element 16 is a variable resistor. With the same input voltage $V_{in}$, an output voltage $V_{out}$ can vary with the resistance value of the piezoresistive element 16.

Figure 3A:
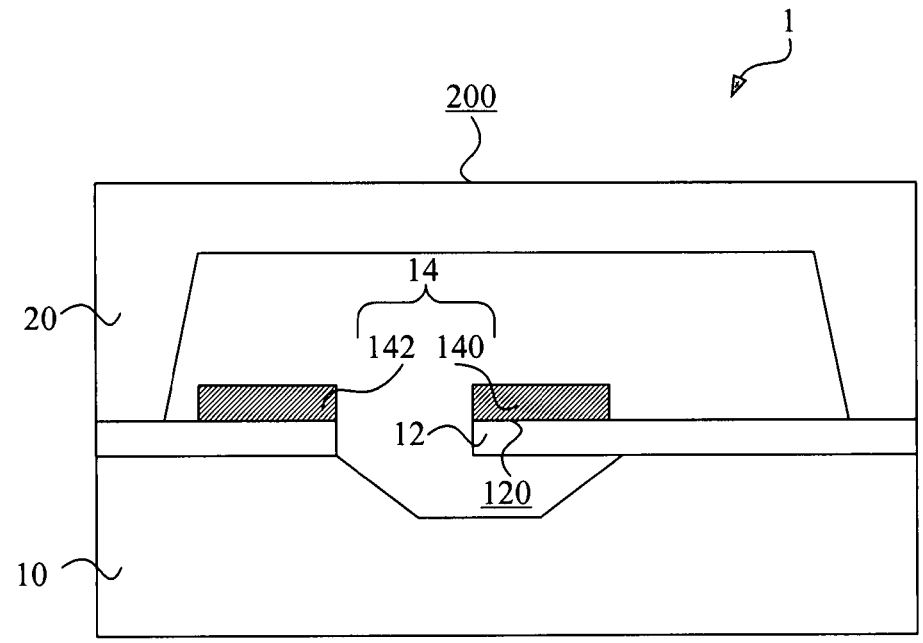
FIG. 3A is a micro-sensor according to another embodiment of the invention.

Please refer to FIG. 3A. FIG. 3A is a micro-sensor 1 according to another embodiment of the invention.

As shown in FIG. 3A, the micro-sensor 1 can further include a casing 20. The casing 20 can include a reaction chamber which the micro-cantilever 12 is installed in and a fluid containing chemical substances flows into.

In practical applications, the casing 20 can be formed of a glass, a polymer or a semiconductor material. In one embodiment, the casing 20 can be formed of polydimethylsiloxane (PDMS).

Figure 3B:
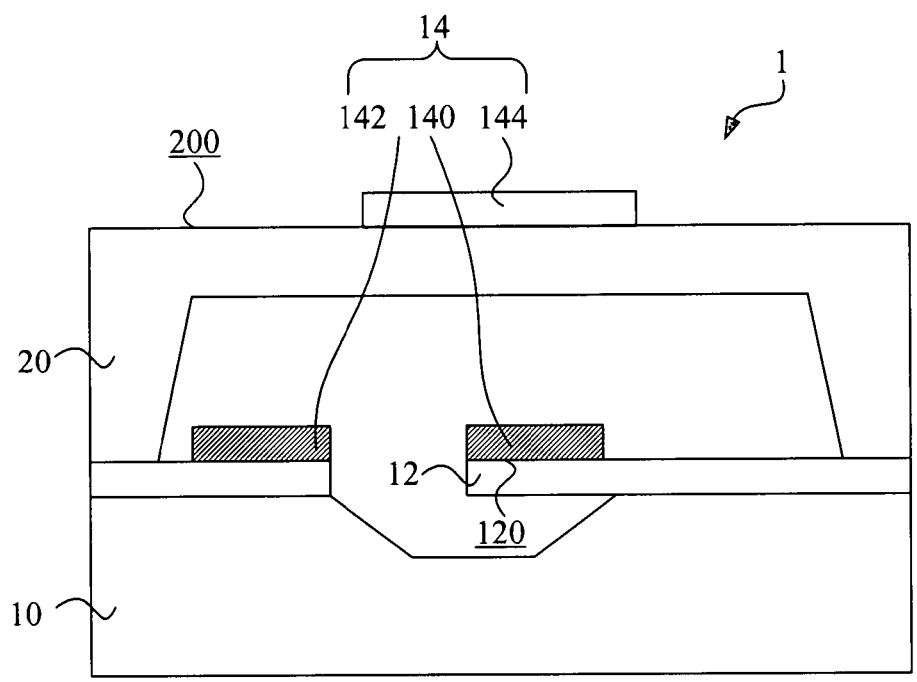
FIG. 3B is a micro-sensor according to another embodiment of the invention.

Please refer to FIG. 3B. FIG. 3B is a micro-sensor 1 according to another embodiment of the invention.

As shown in FIG. 3B, the electrode structure 14 can further include a third electrode 144 formed on an upper surface 200 of the casing 20. In one embodiment, the third electrode 144 can be a transparent electrode. For example, the third electrode 144 can be formed of ITO.

Compared to the prior art, with the electrical field provided by the electrode structure, the micro-sensor according to the invention can not only increase the immobilization efficiency of probing proteins on the capturing surface of the micro-cantilever but also reduce the consumption of biochemical samples.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A micro-sensor for sensing a chemical substance, said micro-sensor comprising:
    a substrate;
    a micro-cantilever formed on the substrate and having a capturing surface on a top surface of the micro-cantilever for capturing the chemical substance;
    an electrode structure for supplying an electrical field, the electrical field being disposed so as to assist the capturing surface in capturing the chemical substance; and
    a measuring device, coupled to the micro-cantilever, for measuring a variation on a mechanical property of the micro-cantilever induced by the captured chemical substance and interpreting the variation on the mechanical property of the micro-cantilever into an information relative to the chemical substance.

2. The micro-sensor of claim 1, wherein the electrical field is a DC electrical field for assisting the capturing surface in capturing the chemical substance.

3. The micro-sensor of claim 2, wherein the electrical field is further an AC electrical field for assisting the chemical substance in escaping from the capturing surface.

4. The micro-sensor of claim 1, further comprising:
    a casing comprising a reaction chamber which the micro-cantilever is installed in and a fluid containing the chemical substance flows into.

5. The micro-sensor of claim 2, wherein the casing is formed of a material selected from the group consisting of a glass, a polymer and a semiconductor material.

6. The micro-sensor of claim 5, wherein the casing is formed of polydimethylsiloxane.

7. The micro-sensor of claim 4, wherein the electrode structure comprises a first electrode formed on the capturing surface of the micro-cantilever, and a second electrode formed on the substrate.

8. The micro-sensor of claim 7, wherein the first electrode is formed of gold, and the second electrode is formed of nickel.

9. The micro-sensor of claim 7, wherein the electrode structure further comprises a third electrode formed on an upper surface of the casing.

10. The micro-sensor of claim 1, wherein a portion of the micro-cantilever is doped to form a piezoresistive element, and at least one resistor of the measuring device and the piezoresistive element constitute an electric bridge with which the measuring device measures the variation on the mechanical property of the micro-cantilever.

11. The micro-sensor of claim 1, wherein the substrate is formed of silicon.

12. The micro-sensor of claim 11, wherein the micro-cantilever is formed of $Si_3N_4$ or $SiO_2$.

13. The micro-sensor of claim 1, wherein the chemical substance is one selected from the group consisting of a metal, a polymer, a biochemical molecule, and a micro-biochemical structure.

* * * * *